(12) United States Patent
Kim et al.

(10) Patent No.: US 7,959,932 B2
(45) Date of Patent: Jun. 14, 2011

(54) HUMAN ROTAVIRUS AND VACCINE COMPOSITION COMPRISING SAME

(75) Inventors: Wonyong Kim, Seoul (KR); Inseok Lim, Seoul (KR); Le Van Phan, Seoul (KR); Sun-Woo Nam, Seoul (KR); Jung-Hoon Yoon, Daejeon-si (KR)

(73) Assignee: Chung-Ang University Industry Academic Cooperation Foundation, Seoul (KR)

( * ) Notice: Subject to any disclaimer, the term of this patent is extended or adjusted under 35 U.S.C. 154(b) by 34 days.

(21) Appl. No.: 12/443,071

(22) PCT Filed: Sep. 28, 2007

(86) PCT No.: PCT/KR2007/004751
§ 371 (c)(1),
(2), (4) Date: Mar. 26, 2009

(87) PCT Pub. No.: WO2008/039022
PCT Pub. Date: Apr. 3, 2008

(65) Prior Publication Data
US 2010/0047278 A1    Feb. 25, 2010

(30) Foreign Application Priority Data
Sep. 28, 2006    (KR) .................. 10-2006-0094867

(51) Int. Cl.
*A61K 39/15*    (2006.01)
(52) U.S. Cl. ..................................... 424/215.1
(58) Field of Classification Search .......... None
See application file for complete search history.

(56) References Cited

U.S. PATENT DOCUMENTS

| | | | | |
|---|---|---|---|---|
| 6,673,355 B1 * | 1/2004 | Estes et al. | ................. | 424/215.1 |
| 7,285,280 B1 * | 10/2007 | Colau et al. | ................. | 424/215.1 |
| 2002/0058043 A1 | 5/2002 | Hoshino et al. | | |

OTHER PUBLICATIONS

NCBI Genbank Accession No. AB269689, Aug. 15, 2006, See ISR and Written Opinion of the ISA.
NCBI Genbank Accession No. DQ321496, Jan. 1, 2006, See ISR and Written Opinion of the ISA.
NCBI Genbank Accession No. AJ236774, Apr. 15, 2005, See ISR and Written Opinion of the ISA.
NCBI Genbank Accession No. AB269689, Aug. 15, 2006.
NCBI Genbank Accession No. DQ321496, Jan. 1, 2006.
NCBI Genbank Accession No. AJ236774, Apr. 15, 2005.
Penelope H. Dennehy, "Rotavirus Vaccines: an Update," Current Opinion Pediatrics, 2005, vol. 17, pp. 88-92.
Tzipori et al., "Studies on Attenuation of Rotavirus: A Comparison in Piglets Between Virulent Virus and its Attenuated Derivative," Archives of Virology, 1989, vol. 109, pp. 197-205.
Gentsch et al., "Serotype Diversity and Reassortment Between Human and Animal Rotavirus Strains: Implications for Rotavirus Vaccine Programs," The Journal of Infectious Diseases, 2005, vol. 192, pp. S146-159.

* cited by examiner

*Primary Examiner* — Ali R. Salimi
(74) *Attorney, Agent, or Firm* — Sughrue Mion, PLLC (57) ABSTRACT

Provided are G12 human rotaviruses having VP7 gene of SEQ ID NO: 1 or 2 and VP4 gene of SEQ ID NO: 3 or 4; antibodies specific for said rotaviruses; and a vaccine composition containing the same. The antibodies and the vaccine composition are effective for diagnosing rotavirus infection and for treatment of diseases caused by rotavirus.

3 Claims, 9 Drawing Sheets

|        | CAU 195 | CAU 214 | L26  | T152 | CP727 | CP1030 | Se585 | HC91 |
|--------|---------|---------|------|------|-------|--------|-------|------|
| CAU 214| 99.5    |         |      |      |       |        |       |      |
| L26    | 90.3    | 89.5    |      |      |       |        |       |      |
| T152   | 97.7    | 96.2    | 90.5 |      |       |        |       |      |
| CP727  | 97.7    | 97.1    | 91.0 | 99.4 |       |        |       |      |
| CP1030 | 97.5    | 97.0    | 91.0 | 99.3 | 99.3  |        |       |      |
| Se585  | 99.2    | 98.6    | 90.2 | 97.8 | 97.8  | 97.7   |       |      |
| HC91   | 97.6    | 97.0    | 90.6 | 99.4 | 99.4  | 99.3   | 98.0  |      |
| RU172  | 89.5    | 89.2    | 91.8 | 89.4 | 89.5  | 89.6   | 89.8  | 89.1 |

HUMAN ROTAVIRUS AND VACCINE COMPOSITION COMPRISING SAME

This is a national stage application under 35 U.S.C. §371 of PCT/KR2007/004751 filed on Sep. 28, 2007, which claims priority from Korean patent application 10-2006-0094867 filed on Sep. 28, 2006, all of which are incorporated herein by reference.

FIELD OF THE INVENTION

The present invention relates to a human rotavirus having VP7 gene represented by SEQ ID NO: 1 or 2 and VP4 gene represented by SEQ ID NO: 3 or 4.

BACKGROUND OF THE INVENTION

Rotavirus is a major cause of diarrhea in infants and young children throughout the world (World Health Organization: WHO WER 74:33-38, 1999). CDC (Center for Disease Control and Prevention) has reported that every year 440,000 infants and young children under 5 years of age die due to rotavirus infection. Under this circumstance, WHO has declared that the development of an anti-rotavirus vaccine is a project of the highest priority (Glass R I et al., *Science* 265:1389-1391, 1994). It has been reported that the situation in Korea is similar to the world-wide trend: rotavirus is the most common cause of diarrhea in infants and young children (Kim K H et al., *J Clin Microbiol* 28: 2279-2284, 1990).

The rotavirus belongs to Reoviridae family and has no envelope. Further, it has icosahedral shape having a diameter of 75 nm and consists of triple capsid proteins, i.e. outer, inner and core capsids (Estes M K & Cohen J: *Microbiol Rev* 53: 410-449, 1989). The genome of the rotavirus consists of double strand RNA segments which encode 11 rotavirus proteins, i.e., 6 structural proteins (VP1, VP2, VP3, VP4, VP6 and VP7) and 6 non-structural proteins (NSP1, NSP2, NSP3, NSP4, NSP5 and NSP6. The outer capsid includes VP4 and VP7 associated with pathogenicity, immunogenicity, cellular adhesiveness and intrusion of the rotavirus. VP6 lied in the inner capsid is a major structural protein which surrounds core part of the rotavirus and has been employed for diagnosing the virus infection as it is a common antigen of rotaviruses (Kohli E et al., *Virology* 194:110-116, 1993).

The rotavirus is divided into seven groups, A to G. Group A rotavirus is further divided into G-type (glycoprotein type) based on immunogenic protein VP7 and P-type (protease-sensitive protein) based on the immunogenic protein VP4 (Gentsch J R et al., *J Infect Dis* 174 suppl. 1: S30-S36, 1996). 16 G serotypes and at least 27 P genotypes have been identified until now. In human, 9 serotypes, i.e., G1 to G4, G6, G8 to G10 and G12, and 8 genotypes, i.e., P[3], P[4], P[6], P[8] to P[11] and P[14] are known to cause the viral infection (Rahman M et al., *J Clin Virol* 33:1-6, 2005; Santos N & Hoshino Y: *Rev Med Virol* 15: 29-56, 2004).

It is not an easy task to develop a new vaccine which effectively works on all the identified infection serotypes (Glass R I et al., *J Infect Dis* 192 Suppl 1:S160-166, 2005). An attenuated rotavirus vaccine for oral administration (cow, UK, WC3; monkey, SA11, MMU18006; human, M37) and an animal-human recombinant vaccine also show insufficient protection from other serotypes (Anderson E L et al., *J Infect Dis* 153:823-831, 1986; Bernstein D I et al., *JAMA* 273:1191-1196, 1995; Clark H F et al., Am J Dis Child 140:350-356, 1986; Conner M E et al., *Curr Top Microbiol Immunol* 105: 253, 1994; De Mol P. et al., *Lancet II* 108. 1986; Flores J, et al., *J Clin Microbiol* 27: 512-518, 1988; Kapikian A Z et al., *Adv Exp Med Biol* 257:67, 1990; Rennels M B et al., *Pediatrics* 97:7-13, 1996; Vesikari T, *Vaccine* 11:255-261, 1993). Recently, Wyeth-Ayerst (USA) has developed a tetravalent attenuated rotavirus vaccine, Rotashield®, which contains the most common rotavirus serotypes in the world, G1 to G4. Rotashield® was approved by the US Food and Drug Administration (FDA) and it is incorporated in a basic vaccination which is to be administered to children at 2, 4, and 6 months of age. However, FDA's approval of Rotashield® was canceled due to 15 cases of intussusception (Murphy T V et al., *N Engl J Med* 344:564-572, 2001). Further, an increasing number of atypical serotypes which seldom appear in human have recently been found to infect children, and a particular rotavirus of G12 serotype has also been reported to be prevalent in Tailand (Pongsuwanna Y et al., *J Clin Microbiol* 40:1390-1394. 2002), United States (Griffin D D et al., *Virology* 294: 256-269, 2002), India (Das S et al., *J Clin Microbiol* 41:2760-2762, 2003), Japan (Shinozaki K et al., *J Med Virol* 73:612-616, 2004), Argentina, and South Korea (Santos N & Hoshino Y, *Rev Med Virol* 15:29-56, 2004). However, most of G12 rotaviruses were identified by detection of G12 gene from a stool using RT-PCR. Hitherto, G12 rotaviruses: L26 of G12 (Japan, 1990), Se585 of G12P2A[6] (USA, 2002), T152 of G12P[9] (Thailand, 2003), CP727 and CP1030 of G12P[9] (Japan, 2004) and HC91 of G12P[9] (Brazil, 2006) were isolated from human, and RU172 of G12P[7] (India, 2006), from pigs.

The present inventors have therefore endeavored to find a new G12 human rotavirus and prepared a new vaccine composition comprising same.

SUMMARY OF THE INVENTION

Therefore, it is an object of the present invention to provide a new G12 human rotavirus.

It is another object of the present invention to provide an antibody specific for said new G12 human rotavirus and a composition comprising same for diagnosing rotavirus infection.

It is a further object of the present invention to provide a vaccine composition for preventing or treating a disease caused by rotavirus infection and a process for the preparation thereof.

In accordance with one aspect of the present invention, there is provided a human rotavirus comprising VP7 gene of SEQ ID NO: 1 or 2 and VP4 gene of SEQ ID NO: 3 or 4.

In accordance with another aspect of the present invention, there is provided an antibody specific for the human rotavirus and a composition comprising same for diagnosing rotavirus infection.

In accordance with a further aspect of the present invention, there is provided a vaccine composition comprising the attenuated rotavirus or inactivated human rotavirus and a pharmaceutically acceptable carrier and process for preparation thereof.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

The human rotavirus of the present invention comprises V7 gene represented by SEQ ID NO: 1 or 2 and VP4 gene represented by SEQ ID NO: 3 or 4.

VP7 gene and VP4 gene in the rotavirus constitute an outer capsid of the rotavirus and are associated with pathogenicity, immunogenicity, cellular adhesiveness and intrusion of the rotavirus. G serotype and P genotype of the rotavirus are classified based on VP7 gene and VP4 gene, respectively.

In an embodiment of the present invention, the result of seminested multiplex PCR analysis for VP7 gene and VP4 gene of the rotavirus obtained from the stool specimens of the children suffering from the rotavirus infection shows that G serotype and P genotype of the inventive rotavirus are G12 and P[6], respectively. VP7 gene and VP4 gene of the inventive rotavirus are represented by SEQ ID NO: 1 or 2 and SEQ ID NO: 3 or 4, respectively.

Further, the human rotavirus of the present invention comprises NSP4 gene represented by SEQ ID NO: 5 or 6.

NSP4 gene, which plays an important role in the pathogenicity of the rotavirus, increases the level of cAMP or cGMP by binding to specific receptors which exist in the intestinal canal and cause diarrhea by activating cyclic nucleotide signaling pathway, inducing increased Cl⁻ secretion and decreased absorption of Na⁺ and water. Therefore, the characteristics of NSP4 gene must be examined based on its pathogenicity. For the present, NSP4 gene can be divided into 4 genotypes, i.e. NSP4[A], NSP4[B], NSP4[C] and NSP4[D] according to their nucleotide sequences.

In an embodiment of the present invention, gene sequencing of NSP4 genotype of the inventive rotaviruses was conducted and it has been found that NSP4 genotype of the inventive rotaviruses is NSP4[B]. NSP4 gene of the inventive rotavirus is represented by SEQ ID NO: 5 or 6.

The present inventors isolated and identified human rotavirus strains having the above-mentioned characteristics, which were named as CAU 195/G12 and CAU 214/G12 and deposited on Sep. 19, 2006 with Korean Collection for Type Cultures (KCTC) (address: Korea Research Institute of Bioscience and Biotecnology (KRIBB), #52, Oun-dong, Yusong-ku, Taejon 305-333, Republic of Korea) with the accession Nos. KCTC 10988BP and KCTC 10989BP, respectively.

Further, the present invention provides an antibody specific for the inventive rotavirus strains. The antibody may be polyclonal, monoclonal or humanized ones.

In one embodiment of the present invention, animals are immunized with the inventive rotavirus strains, CAU 195/G12 and CAU 214/G12, as antigens to prepare antibodies specific for them. The antigens are administrated to the test animals' abdominal cavity, muscles, eyes or subcutis according to the ordinary immunization method. If necessary, various other techniques may be used to enhance the immune response and to make the antibody reactivity much stronger. For instance, Freund's complete adjuvant or incomplete adjuvant may be used to increase the immunity of the inventive antibody.

The antibody of the present invention is useful for diagnosis or detection of G12 human rotavirus due to its specificity for such rotavirus.

Furthermore, the present invention provides a composition comprising the antibody for diagnosing a disease caused by rotavirus infection.

The inventive composition may further comprise a reagent commonly used in immunological analysis. The reagent may be a suitable carrier used in ordinary quantitative analysis based on an antigen-antibody reaction, a marker which can generate a detectable signal, solvent or detergent. The quantitative analysis method may be immunoblot, immunoprecipitation, enzyme-linked immunoabsorbent assay, protein chips, rapid assay or microarray.

The carrier may be a soluble carrier, e.g., any one of physiologically acceptable buffer solutions used in the relevant art, or an insoluble carrier, e.g., polystyrene, polyethylene, polypropylene, polyester, polyacrylonitrile, fluoric resin, crosslinked dextran, polysaccharide, glass, metal, agarose and a mixture thereof.

The marker may be an enzyme, a fluorescent material, a luminous material or a radioactive material. The enzyme may be peroxidase, alkaline phosphatase, β-D-galactosidase, glucose oxidase, malate dehydrogenase, glucose-6-phosphodehydrogenase or invertase, and the fluorescent material may be fluorescein isothiocyanate, phycobilin, rhodamine, phycoerythrin, phycocyanin or orthophthalic aldehyde. The luminous material may be isolumino or lucigenin, and the radioactive material may be $^{131}I$, $^{14}C$ or $^{3}H$. Further, any other carriers and markers which can be used in immunological analysis may be employed in the present invention.

The present invention also provides a vaccine composition comprising attenuated or inactivated inventive human rotavirus and a pharmaceutically acceptable carrier, which is capable of stimulating the generation of a neutralizing antibody specific for G12 human rotavirus.

Specifically, the rotavirus of the present invention may be used in preparing the vaccine composition for preventing a disease caused by rotavirus infection. For example, a killed vaccine may be prepared by inactivating the inventive rotavirus, viruses having substantially identical characteristics with the inventive rotavirus, or variants thereof; and an attenuated vaccine may be prepared by sub-culturing the above-mentioned viruses or variants in a cell or an animal. Further, a vaccine comprising viral antigens may be prepared by using viral antigenic proteins produced in a large quantity by conventional genetic recombination methods, employing modified viral genes encoding the viral antigenic proteins. Such modified viral genes may be used as a recombinant DNA vaccine. A synthetic vaccine may be prepared by using chemically synthesized viral antigens or their specific motifs of the virus or its variant.

The inventive vaccine composition may be administered orally or intranasally. It is preferable to administer the attenuated rotavirus vaccine via oral or intranasal routes. The inactivated rotavirus vaccine may preferably be administered parenterally, for example, intramuscular injection. The vaccine composition may be dispersed in an injection medium such as edible oils, e.g., corn oil, olive oil, soy bean oil, safflower oil, cotton seed oil, peanut oil, sesame oil and sunflower oil; mineral oil; squalene; sqalane; cod liver oil; mono-, di- and tri-glyceride; and a mixture thereof. If necessary, the injection solution may further comprise a dispersing agent or an antiseptic. The vaccine composition of the present invention can be administered in a single dose, or in multiple doses based on fractionated treatment protocol. Further, the dose of the active ingredient actually administered may vary in light of the severity of disease and, generally, an operative dose of the active ingredient ranging from $1 \times 10^2$ to $1 \times 10^4$ pfu can be administered several times per day. It should be understood that the amount of the active ingredient actually administered to a certain patient ought to be determined in light of various relevant factors including the frequency of administration, the body weight, age, sex, health condition, diet and excretion rate of the individual patient, the chosen route of administration or the severity of the patient's symptom. The inventive vaccine composition is not limited with respect to its formulation, route and manner of administration as long as being effective.

The present invention also provides a process for preparing of a human rotavirus vaccine comprising the steps of:

1) allowing the human rotavirus having VP7 gene represented by SEQ ID NO: 1 or 2 and VP4 gene represented by SEQ ID NO: 3 or 4 to proliferate in a host cell; and 2) attenuating or inactivating the proliferated human rotavirus obtained in step 1.

In step 2, the virus may be inactivated by heating a supernatant obtained by centrifuging the culture medium containing the host cell. Further, in order to prevent possible environmental pollution caused by the rotavirus, the supernatant may be subjected to formalin treatment and removal of formalin, before heating.

The following Examples are intended to further illustrate the present invention without limiting its scope.

Example 1

Isolation of Human Rotaviruses

<1-1> Identification of P Genotype of Rotaviruses Isolated from Stool Specimens

Stool specimens obtained from 452 children infected by rotavirus and hospitalized in Chung-Ang University Yongsan Hospital in Seoul, South Korea were subjected to seminested multiplex PCR (Gouvea et al., *J Clin. Microbiol.* 28:276-282, 1990; 32:1338-1340, 1994) to identify P genotype.

The result of the seminested multiplex PCR analysis for VP4 gene showed that P genotype of the rotavirus was P[6] as shown in FIG. 1, while those for VP7 gene were two viruses without identifying G serotype thereof as shown in FIG. 2.

<1-2> Identification of G Serotype of the Two Rotaviruses by Sequencing G7 Gene

VP7 gene was amplified by RT-PCR and subjected to gene sequencing to identify G serotype of the two viruses untyped in <1-1>, as follows. Further, VP4 gene and NSP4 gene were also subjected to RT-PCR and gene sequencing.

First, the stool specimens obtained in <1-1> were treated with TRI Reagent (Molecular Research Center, Cincinnati, USA) to extract viral RNA and then, in 20 ng of the extracted RNA 7% DMSO was mixed with. The mixture was heated at 100° C. for 5 minutes, and an RT-PCR reaction solution (10× Taq buffer, 0.2 mM dNTPs, 1.5 mM $MgCl_2$, 1 μM forward primer, 1 μM reverse primer, 4 U AMV reverse transcriptase) and 11 μM of 2.5 U Tag polymerase (Roches, Indianapolis, USA) were added thereto. Then, the mixture was reacted at 42° C. for 30 minutes to synthesize cDNA of genes VP7, VP4 and NSP4, and subjected to 25 cycles using DNA thermal cycler (Model 480, Perkin-Elmer, Norwalk, USA) for the reactions of, wherein each cycle consisted of the reactions at 94° C. for 1 minute, at 42° C. for 2 minutes, and at 72° C. for 1 minute, and a final reaction at 72° C. for 7 minutes. The amplified VP7, VP4 and NSP4 genes were subjected to electrophoresis on 1.5% SeaKem LE agarose gel (FMC Bioproducts, Rockland, USA) with 0.5× TAE buffer (40 mM Tris-acetate, 2 mM EDTA, pH 8.0) at 100 V for 1 hour (FIG. 3). The primers and their sequences employed in the above procedure are shown in Table 1.

For the DNA sequencing, 50 ng of the amplified DNA of VP7, VP4 and NSP4 were analyzed with BigDye terminatior cycle sequencing kit (Applied Biosystems, Norwalk, USA) using ABI PRISM 310 Genetic Analyzer (Perkin-Elmer, Norwalk, USA). The DNA sequence of VP7 gene was determined using ABI PRISM DNA Sequencing analysis (version 3.3) software (Perkin-Elmer, Norwalk, USA).

TABLE 1

| Amplified gene | | sequence of primers | location | SEQ ID NO. |
|---|---|---|---|---|
| VP7 | forward | GGCTTTAAAGAGAGAATTTCCGTCTGG | 1-28 | 7 |
| | reverse | GGTCACATCATACAATTCTAATCTAAG | 1062-1036 | 8 |
| VP4 | forward | TGGCTTCGCCATTTTATAGACA | 11-32 | 9 |
| | reverse | ATTTCGGACCATTTATAACC | 887-868 | 10 |
| NSP4 | forward | TGGCTTCGCCATTTTATAGACA | 11-32 | 11 |
| | reverse | GGTCACACTAAGACCATTCC | 750-730 | 12 |

The G serotype of the two rotaviruses of the present invention was proven to be G12 as the result of comparing with other G serotypes rotaviruses (G1: WA; G2: DS-1; G3: SA11; G4: Cr117; G5: OSU; G6: IND; G7: PO13; G8: B37; G9: USA; G10: Mc35; G11: YM; G12: L26; and G13: L13) (FIG. 4).

In the above analysis, the sequences of genes VP 7, VP4 and NSP4 have been found to be represented by SEQ ID NO: 1 and 2; SEQ ID NO: 3 and 4; and SEQ ID NO: 5 and 6, respectively.

Example 2

Isolation of G12 Human Rotaviruses

The two rotaviruses, which were determined to have G12 serotype and P[6] genotype in Example 1, were isolated and purified according to the method of Nakagomi et al. (Nakagomi et al., J. Arch. Virol. 127:365-371, 1992). Specifically, the stool specimens were suspended in 5×PBS and filtered through a 0.22 μm filter. Then, the obtained suspensions were infected to MA104 cells (Prof. Linda J Saif, Ohio State University, USA) supplemented with 0.5% pancreatin and cultured in a 5% $CO_2$ incubator until cytopathogenic effect appeared. The proliferated viruses were sub-cultured 2-3 times and subjected to RT-PCR.

The rotaviruses obtained as above were named as CAU 195/G12 and CAU 214/G12, and deposited in a depositary authority as Deposit Accession Nos: KCTC 10988BP and KCTC 10989BP.

Figure 1:
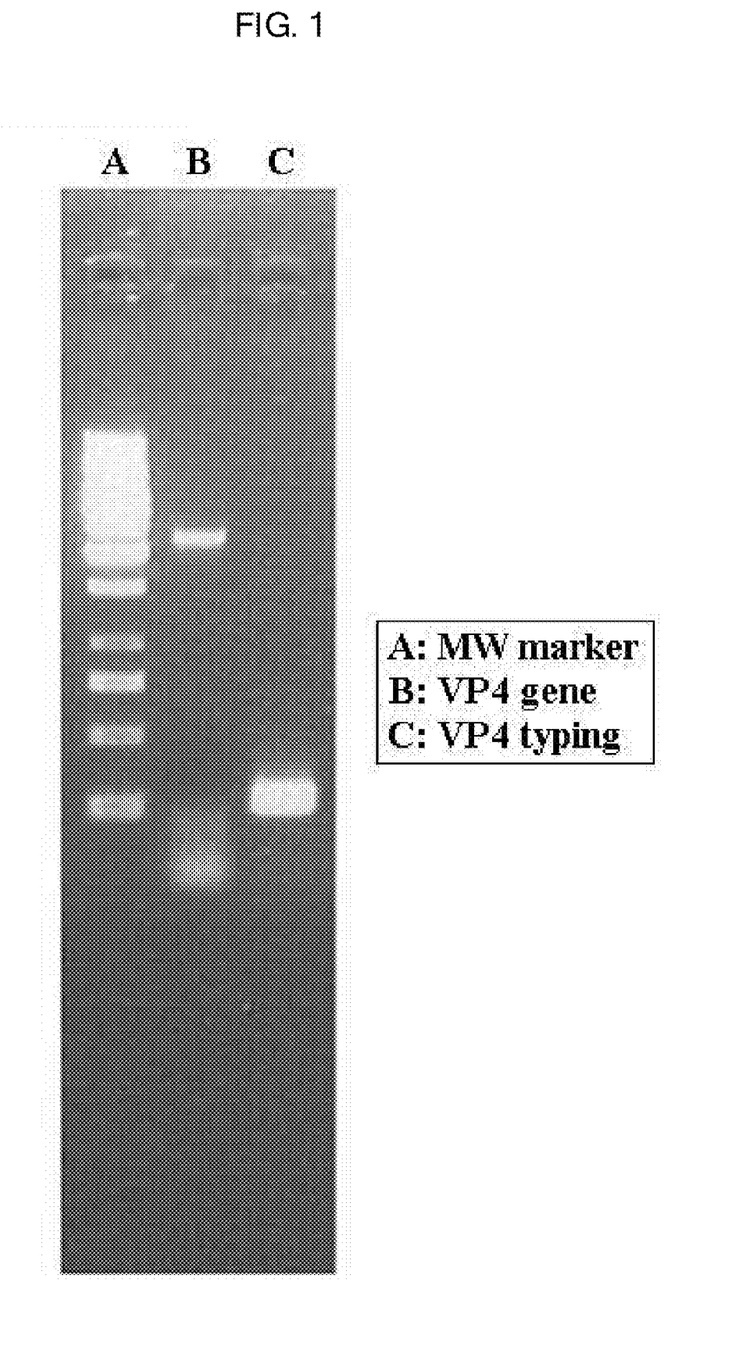
FIG. 1: the result of VP4 gene typing obtained by employing seminested multiplex PCR to identify P genotype of the inventive rotavirus.
Figure 2:
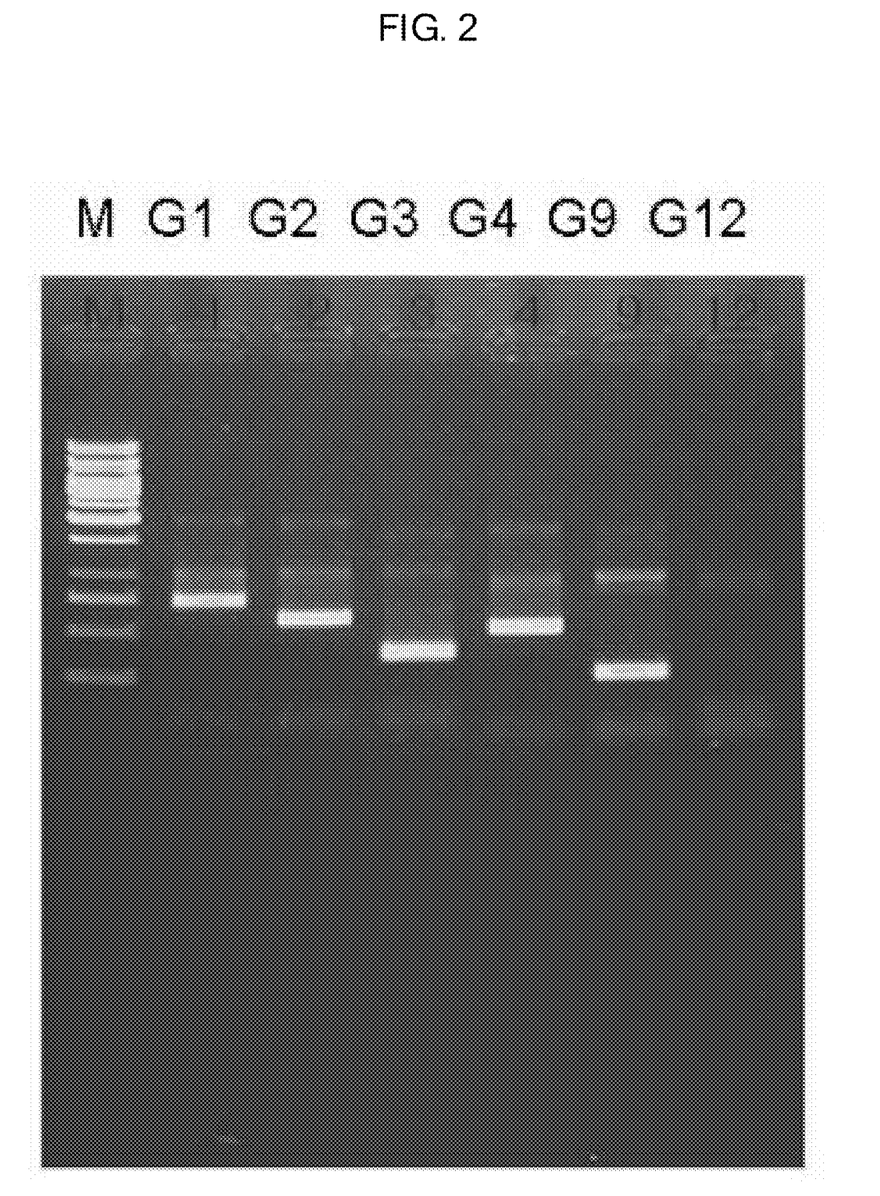
FIG. 2: the result of VP7 gene typing obtained by employing seminested multiplex PCR to identify G serotype of the inventive rotavirus.
Figure 3:
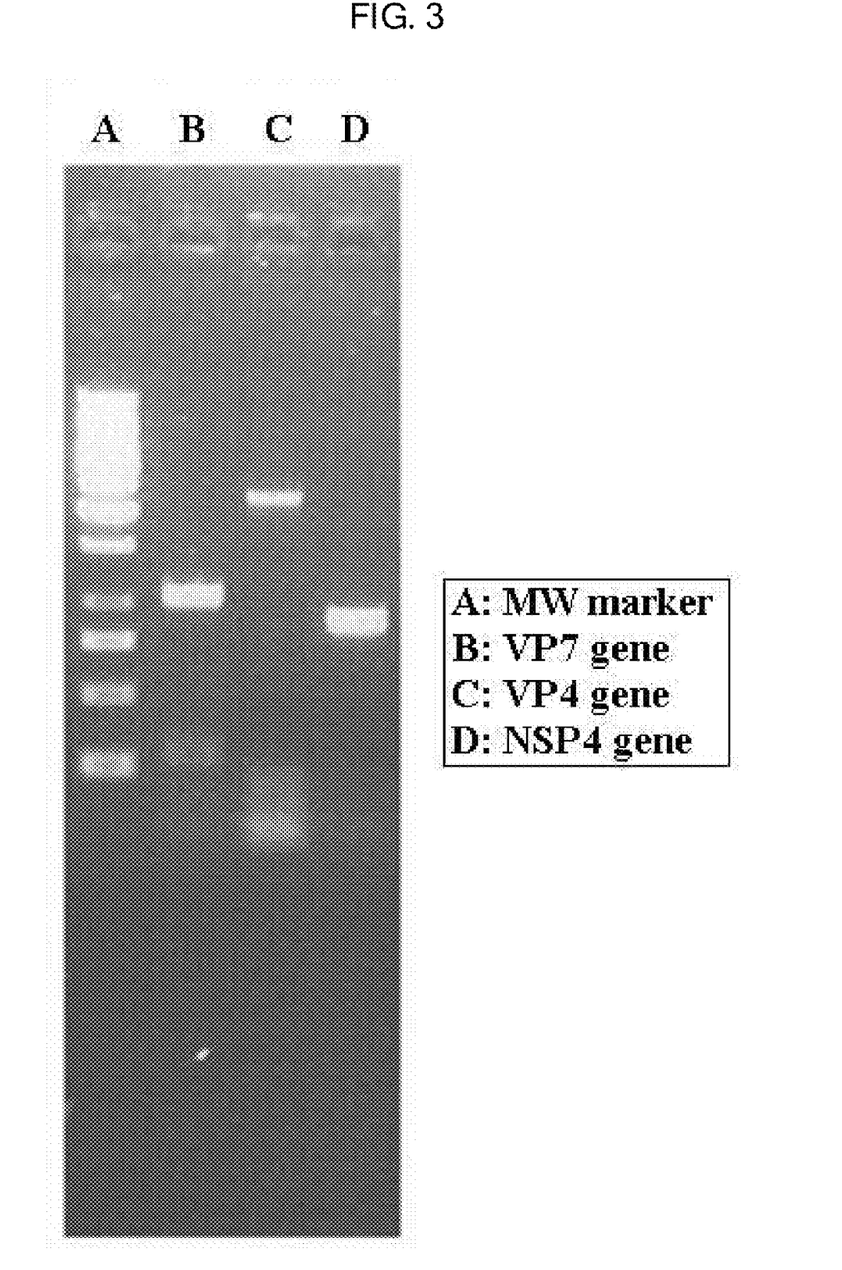
FIG. 3: photographs showing the result of electrophoresis for VP7, VP4 and NSP4 genes of the inventive rotavirus amplified by RT-PCR.
Figure 4:
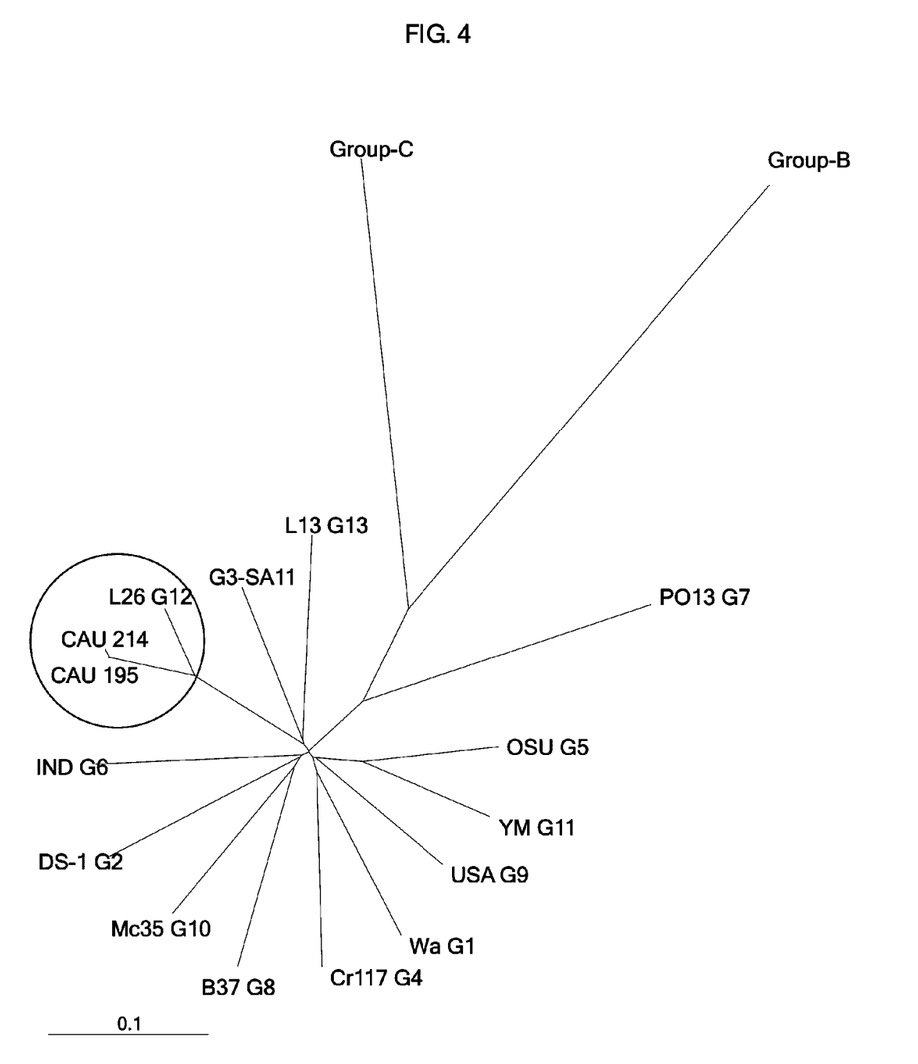
FIG. 4: a phylogenetic tree comparing VP7 gene of the inventive rotavirus with other G serotyperotaviruses (G1: WA; G2: DS-1; G3: SA11; G4: Cr117; G5: OSU; G6: IND; G7: PO13; G8: B37; G9: USA; G10: Mc35; G11: YM; G12: L26; and G13: L13)
Figure 5:
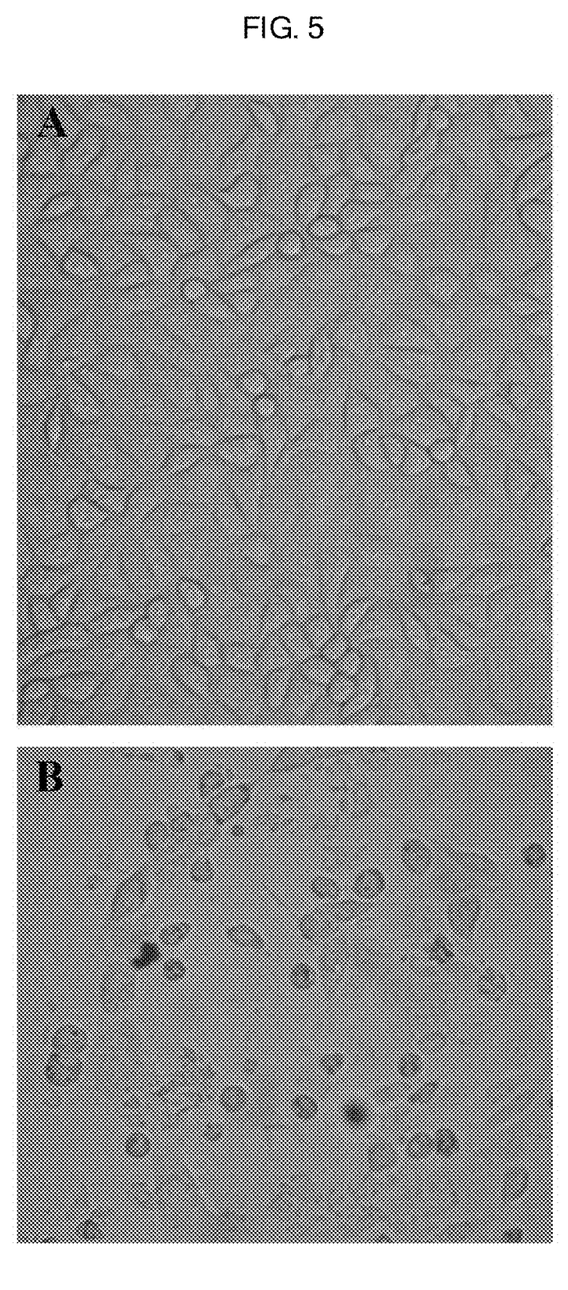
FIG. 5: photographs showing the cytopathogenic effect of the inventive rotavirus obtained from a stool sample with (a) normal MA104 cells and (b) rotavirus infected MA104 cells 24 hours after infection.

FIG. 5 shows the cytopathogenic effect of the subject rotavirus CAU 195/G12.

Example 3

Study for Genetic Interrelation Between G12 Human Rotaviruses

<3-1> Study for Genetic Interrelation Between VP7 gene of G12 Human Rotaviruses

To identify a subclass of CAU 195/G12 and CAU 214/G12, VP7 gene sequences thereof as confirmed in <1-2> were multialigned with those of other G12 rotaviruses, e.g., L26 (Philippine), CP727 and CP1030 (Japan); Se585 (USA); T152 (Thailand); HC91 (Brazil); and RU172 (India), and the result of the multi-alignment was arranged in a similarity matrix using Clustal W (1.7) lo software (Thompson et al., Nucleic Acids Res 22: 4673-4680, 1994). Then, a phylogenetic tree was made based on the similarity matrix using neighbor-joining method (Saitou and Nei, Mol Biol Evo 4: 406-425, 1987).

Figure 6:
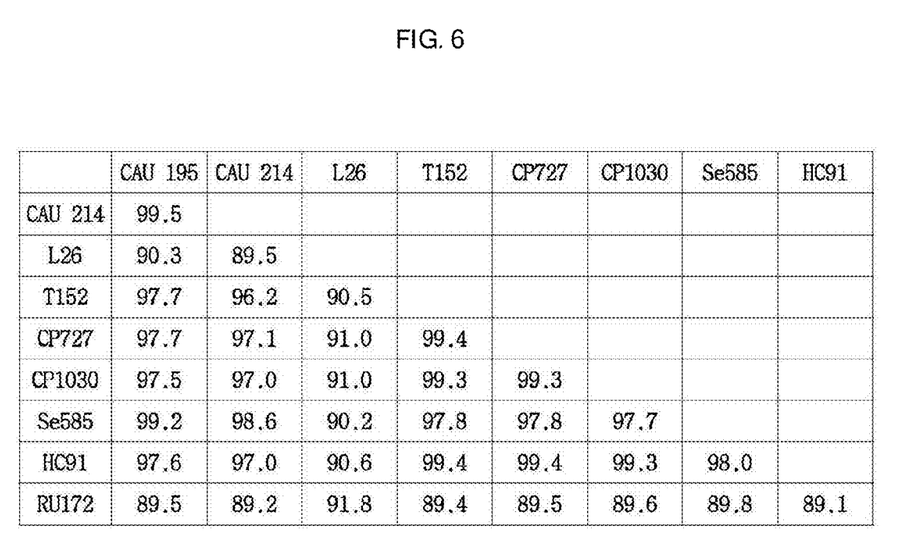
FIG. 6: a similarity matrix representing genetic interrelation among V7 genes of the inventive rotaviruses, CAU 195/G12 and CAU 214/G12; other G12 human rotaviruses, i.e. L26 (Philippine), Se585 (USA), T152 (Thailand), CP727 and CP1030 (Japan), HC91 (Brazil); and swine rotavirus of G12 serotype, RU172 (India)
Figure 7:
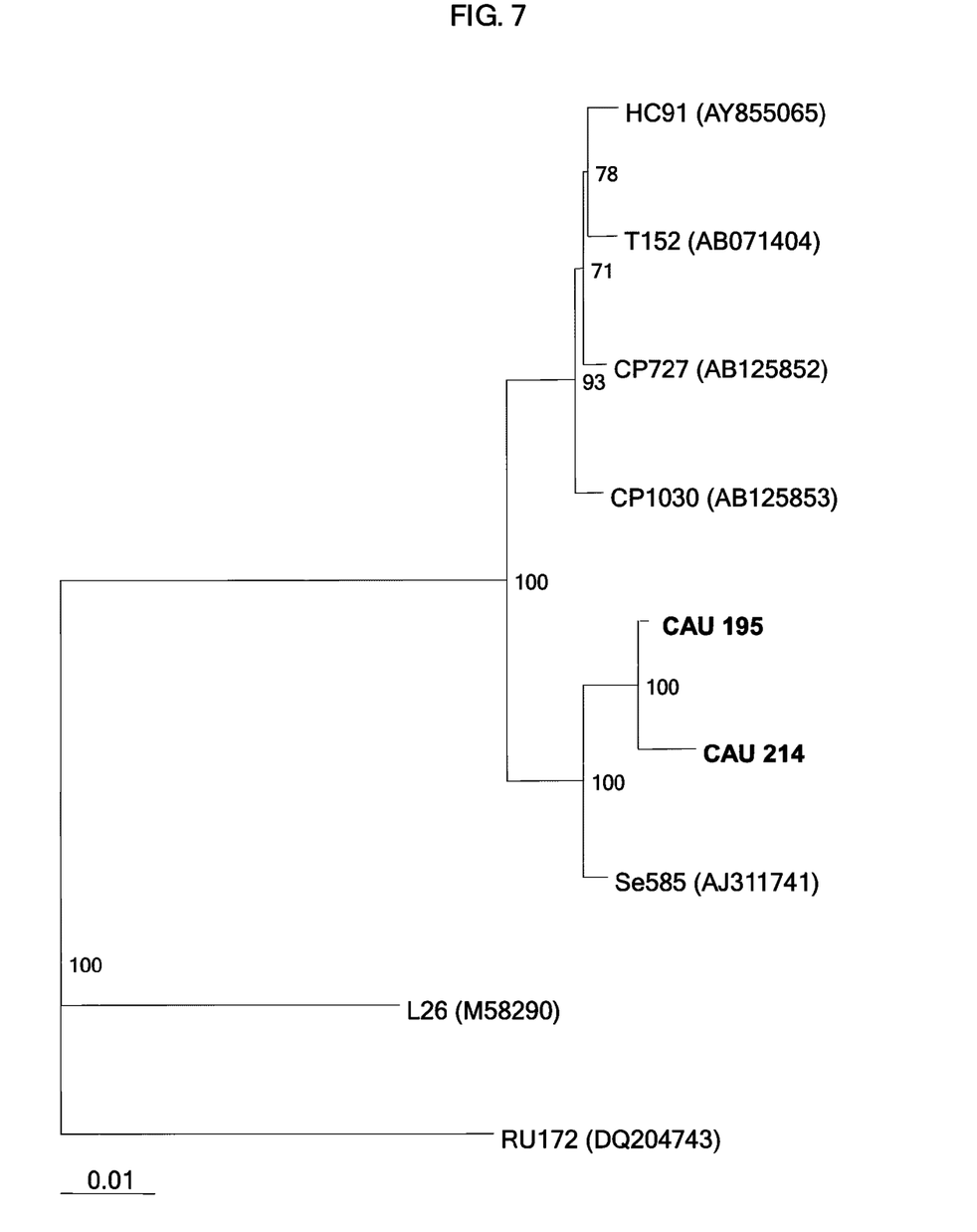
FIG. 7: a phylogenetic tree schematized on the basis of the similarity matrix of FIG. 6.

As presented in FIG. 6, the nucleotide sequences of V7 genes of CAU 195/G12 and CAU 214/G12 showed >90% identity with those of other G12 rotaviruses; 99.5% with each other; 98.6% and 99.2% with Se585 (AJ31174); and 89.5% and 90.3% with L26 (M58290). As also illustrated in FIG. 7, VP7 genes of the subject rotaviruses showed the highest sequence homology with Se585 (AJ31174).

<3-2> Study for Genetic Interrelation Between NSP4 Genes of G12 Human Rotaviruses Genetic interrelation between NSP4 genes of the subject rotaviruses (CAU 195/G12 and CAU 214/G12) and the foreign rotaviruses was examined with the same as manner described in <3-1>.

Figure 8:
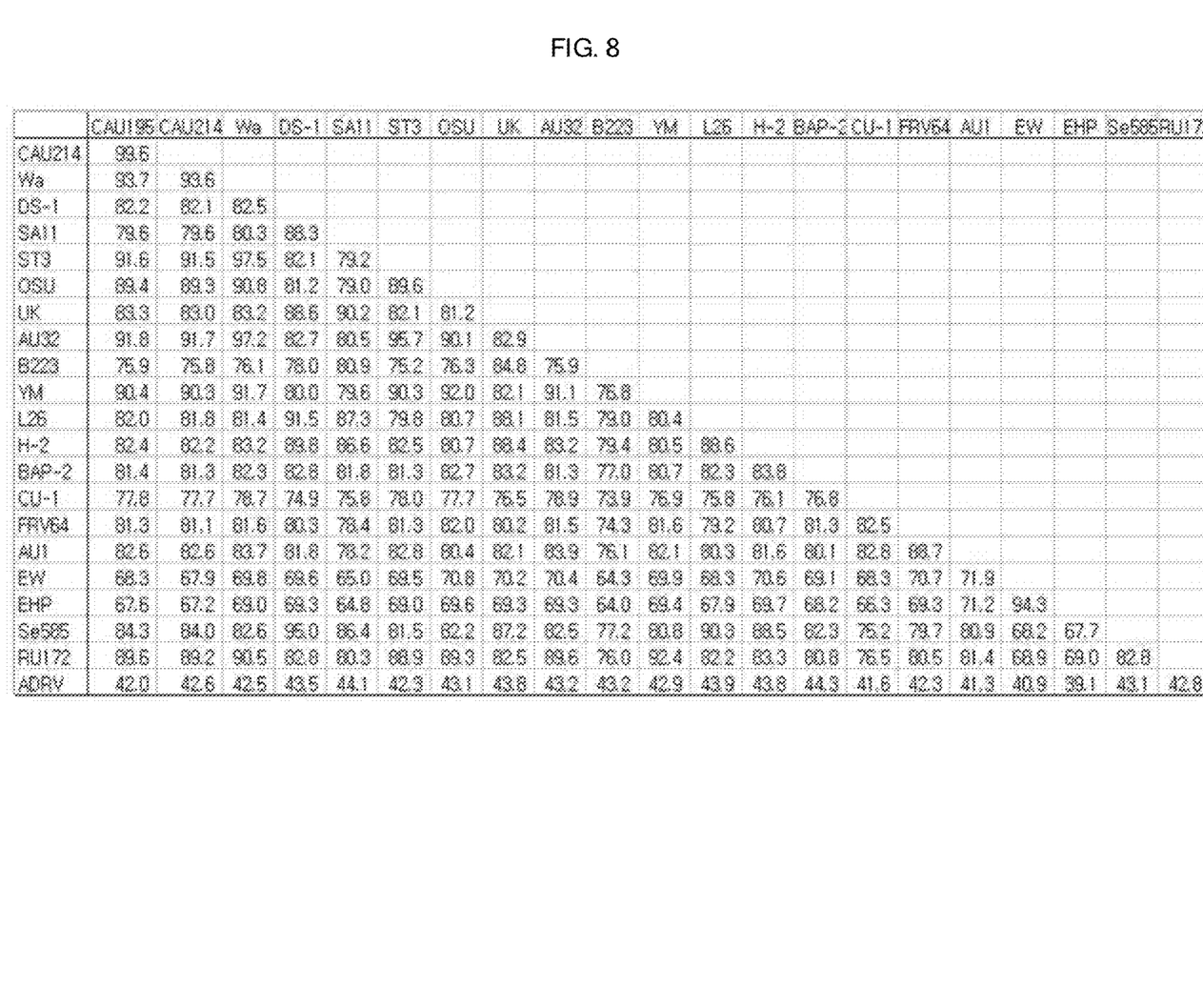
FIG. 8: a similarity matrix representing genetic interrelation among NSP4 genes of the inventive rotaviruses, CAU 195/G12 and CAU 214/G12; and other foreign rotaviruses, i.e. WA, DS-1, SA11, ST3, OSU, UK, AU32, B223, YM, L26, H-2, BAP-2, CU-1, FRV64, AU1, EW, EHP, Se585, RUI72 and ADRV.
Figure 9:
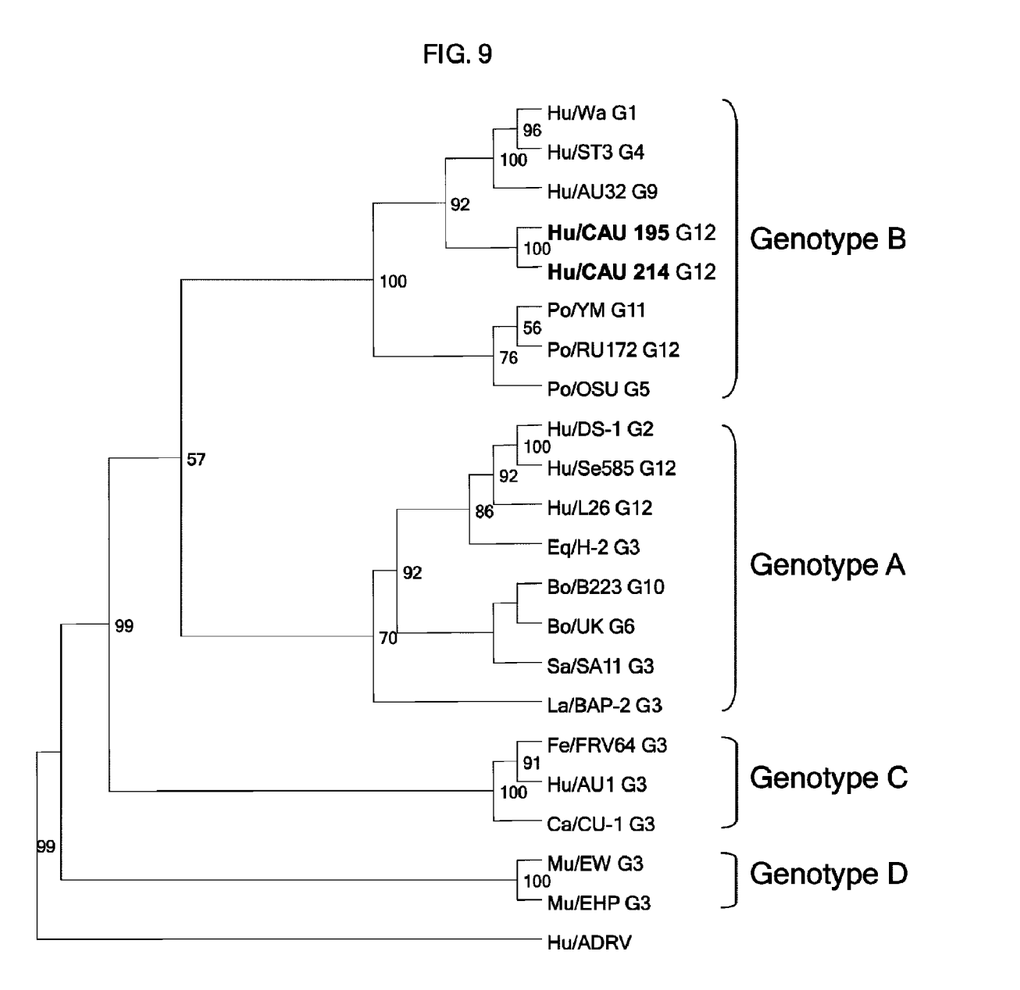
FIG. 9: a phylogenetic tree schematized on the basis of the similarity matrix of FIG. 8.

As the result, FIGS. 8 and 9 demonstrate that NSP4 genes of CAU 195/G12 and CAU 214/G12 belong to NSP4[B] genotype. It is noticeable that NSP4 gene of Se585, which showed the highest sequence homology with the subject rotaviruses, belongs to NSP4[A] genotype.

Example 4

Preparation of G12 Rotavirus Vaccine

MA104 cells were sub-cultured in a T-175 flask. A mixture of CAU 214/G12 infected cells and uninfected cells (1:5) was cultured in a medium, and the supernatant medium was centrifuged at 5,000 rpm for 1 hour when 70% to 80% of the cells were degraded. The supernatant resulting from the centrifugation was treated with 0.01 v % of formalin and inactivated by the incubation in a thermostatic water bath at 37° C. for 10 hours. Then, the supernatant was concentrated by an evaporator, by which formalin was removed therefrom. 20 ml of 30% sucrose was put into the bottom of a centrifuge tube, and the obtained concentrates was added to the top of the tube. Then, the tube was subjected to centrifugation at 100,000 g for 10 hours, and the precipitation of the concentrates which passed through sucrose was obtained. PBS of pH 7.0 was added to the precipitation to flow an antigen out. The protein contents in the precipitation were estimated employing the standard albumin and settled to 50 μg/ml using PBS. After 10 hours heating at 60° C., the resulting solution was filtered through a 0.22 μm sterile filter paper to get stock solution. The vaccine was prepared by diluting the stock solution with PBS to have the final protein contents of 10 μg/ml, and the pH of the vaccine was 7.05.

Example 5

Test for Effectiveness of the Vaccine 0.5 ml of the vaccine prepared in Example 4 was diluted through 4 steps and inoculated to 4 to 5-week-old mouse. 3 weeks after the inoculation, 0.5 ml of the vaccine was inoculated to the mouse again. 3 weeks after the second inoculation, neutralized antibody titer was measured from the serum of the mouse. Blood was taken from the heart of the mouse. The blood was placed at a room temperature for 1 hour, and then in a refrigerator for 24 hours. An effluent from the blood was subjected to centrifugation at 3,000 rpm for 10 minutes, and the supernatant was used as a specimen. The specimen was reacted with 100 pfu of the rotavirus previously prepared, and the resulting mixture was inoculated to MA104 cells. The neutralization of the rotavirus was checked by comparing the inoculated cells with control cells treated only with the rotavirus. The MA104 cells inoculated by the mixture showed 16-fold increase in antibody titer (ED 50: 0.06) for G12 rotavirus and 12-fold increase in antibody titer (ED 50: 0.08) for G4 rotavirus than the control cells, implying that the vaccine prepared in Example 4 induced the formation of effective antibodies for rotaviruses.

Example 6

Preparation of Polyclonal Antibody Specific for Human Rotavirus

CAU 214/G12 rotavirus cultured in MA104 cells was purified by centrifugation at 35,000 rpm for 2 hours with a density gradient of 15, 30 and 60% sucrose. 1 ml (100 pfu) of the purified rotavirus was mixed with Freund's complete adjuvant in the same amount. Then, 0.5 ml of the mixture was inoculated into a femoral muscle of a 4-week-old rabbit. 2 weeks after the inoculation, a mixture of 1 ml (100 pfu) of the rotavirus and Freund's incomplete adjuvant was further inoculated. Another 2 weeks after the second inoculation, the third inoculation was conducted as made in the second inoculation. 2 weeks after the third inoculation, antibody titer was measured in the serum of the rabbit.

While the invention has been described with respect to the above specific embodiments, it should be recognized that various modifications and changes may be made to the invention by those skilled in the art which also fall within the scope of the invention as defined by the appended claims.

What is claimed is:

1. An isolated human rotavirus of G12 serotype, which is CAU 195/G12 (KCTC 10988BP) or CAU 214/G12 (KCTC 10989BP).

2. An immunogenic composition comprising attenuated or inactivated human rotavirus of claim 1 and a pharmaceutically acceptable carrier.

3. A process for preparing a human rotavirus immunogenic composition comprising the steps of:

1) allowing the human rotavirus of claim 1 to proliferate in MA104 cells;

2) harvesting the human rotavirus from the cell culture; and 3) attenuating or inactivating the proliferated human rotavirus obtained in step 1.

* * * * *

SEQUENCE LISTING

<160> NUMBER OF SEQ ID NOS: 12

<210> SEQ ID NO 1
<211> LENGTH: 977
<212> TYPE: DNA
<213> ORGANISM: Human rotavirus
<220> FEATURE:
<221> NAME/KEY: gene
<222> LOCATION: (1)..(977)
<223> OTHER INFORMATION: VP7 gene of human rotavirus CAU 195 strain

<400> SEQUENCE: 1

```
atggtattga atataccaca attctaacct ttttgatatc aattattcta ttaaattata      60
tattaaaatc aataactaat ataatggact ttatcatata tcggttttta ctaatagttg     120
tcgtcatact gccatttatt aaagctcaaa attatggaat aaatcttcca ataacaggtt     180
ctatggatac cgcatatgca aactctacac aacaagagaa ttttatgact tccactttat     240
gcttatatta tccaagttca gtcacgactg aaataactga ccctgattgg acgagcacac     300
tgtcacaact tttcttgact aaaggatggc cgacaaattc cgtctacttc aagagttatg     360
ctgatatatc gtccttctct gtagatccgc agttatattg tgattacaat attgtattaa     420
tacagtacca aaattcatta gcgttagatg tctcagaact tgctgattta attttaaatg     480
aatggttatg taatccgatg gacgtaacgt tgtactatta tcaacaaaca gatgaagcga     540
ataaatggat atcaatggga gaatcatgta cagttaaagt atgtccctta aatacacaaa     600
ctttaggaat tggatgtacg acaaccgacg tcacaacatt tgaagaggta gcaaacgcgg     660
aaaaattagt aataactgac gtcgtggatg gagtcaatca taagattaat attacagtga     720
atacatgtac tatacggaat tgcaaaaaat taggaccgag ggaaaatgta gcaattatac     780
aagtaggtag ttctgacgtc atagacataa cagcagatcc aacaacgatc ccacaaactg     840
aaagaatgat gcgaataaac tggaaaaaat ggtggcaggt gttttatacc gtagtagatt     900
acataaatca aatagttcag gtaatgtcca acgatcaag gtcactaaat tcagctgctt     960
tttactacag aatttag                                                    977
```

<210> SEQ ID NO 2
<211> LENGTH: 983
<212> TYPE: DNA
<213> ORGANISM: Human rotavirus
<220> FEATURE:
<221> NAME/KEY: gene
<222> LOCATION: (1)..(983)
<223> OTHER INFORMATION: VP 7 gene of human rotavirus CAU 214 strain

<400> SEQUENCE: 2

```
tttttgatat caattattct attaaattat atattaaaat caataactaa tataatggac      60
tttatcatat atcggttttt actaatagtt gtcgtcatac tgccatttat taaagctcaa     120
aattatggaa taaatcttcc aataacaggt tctatggata ccgcatatgc aaactctaca     180
caacaagaga attctatgac gtccccatta tgcttatatt atccaagttc agtcacgact     240
gaaataactg accctgattg gacgagcaca ctgtcacaac ttttcttgac taaaggatgg     300
ccgacaaatt ccgtctactt caagagttat gctgatatat cgtccttctc tgtagatccg     360
cagttatatt gtgattacaa tattgtatta atacagtacc aaaattcatt agcgttagat     420
gtctcagaac ttgctgattt aattttaaat gaatggttat gtaatccgat ggacgtaacg     480
ttgtactatt atcaacaaac agatgaagcg aataaatgga tatcaatggg agaatcatgt     540
```

-continued

| | |
|---|---|
| acagttaaag tatgtccctt aaatacacaa actttaggaa ttggatgtac gacaaccgac | 600 |
| gtcacaacat ttgaagaggt agcaaacgcg gaaaaattag taataactga cgtcgtggat | 660 |
| ggagtcaatc ataagattaa tattacagtg aatacatgta ctatacggaa ttgcaaaaaa | 720 |
| ttaggaccaa gggaaaatgt agcaattata caagtaggta gttctgacgt catagacata | 780 |
| acagcagatc caacaacgat cccacaaact gaaagaatga tgcgaataaa ctggaaaaaa | 840 |
| tggtggcagg tgttttatac cgtagtagat tacataaatc aaatagttca ggtaatgtcc | 900 |
| aaacgatcaa ggtcactaaa ttcagctgct ttttactaca gaatttagat atagcttagg | 960 |
| ttagaattgt atgaatgtga cca | 983 |

<210> SEQ ID NO 3
<211> LENGTH: 2261
<212> TYPE: DNA
<213> ORGANISM: Human rotavirus
<220> FEATURE:
<221> NAME/KEY: gene
<222> LOCATION: (1)..(2261)
<223> OTHER INFORMATION: VP4 gene of human rotavirus CAU 195 strain

<400> SEQUENCE: 3

| | |
|---|---|
| cttnagacag ctactcacta attcatacac agttgaatta tcagatgaaa ttaatacaat | 60 |
| tggatcagaa aaaagtcaaa atgtaacgat taatcccgga ccgtttgctc aaacaaatta | 120 |
| tgcaccagtg acttggagtc atggggaagt gaatgattcg acaacgatag agccagtact | 180 |
| cgatggtcct tatcaaccaa caaattttaa gccaccaaac gattactgga tattattgaa | 240 |
| tccaactaat caacaagttg tattagaggg tactaataat actgatattt gggttgcttt | 300 |
| attacttgtt gaaccaaacg taaccaatca agtagacaa tacacattgt ttggagaaat | 360 |
| gaaacaaatt actgtagaaa ataacacaaa caaatggaaa ttcttcgaaa tgttcagaag | 420 |
| taatgttaat gctgaatttc aacataagcg cacattaacg tcagacacta aattagctgg | 480 |
| gtttatgaaa ttttataata gtgtttggac tttccacggt gaaacgccgc atgctacaac | 540 |
| tgattactcg tcaacttcaa atttatctga agtacaaact gtaatacatg ttgagttta | 600 |
| tataatacca agatcgcaag aatctaagtg tagtgaatac ataaatactg ggttaccacc | 660 |
| aatgcagaat acaaggaata tagttccagt tgcgttatca gctagatcag tgacttatca | 720 |
| acgtgctcag gttaatgagg atatcattat atcaaagaca tcgttgtgga agaaatgca | 780 |
| atataacaga gacattataa taaggtttaa atttaataat agtatagtaa aacttggtgg | 840 |
| gctaggttat aaatggtcag aaatttcgtt taaagcggct aattatcagt acagttactt | 900 |
| gcgagatgga gagcaagtta cggcacatac tacttgttca gtcaatggtg tgaataactt | 960 |
| tagttataat ggaggatcac taccaactga ttttagtgta tcaagatatg aagtgattaa | 1020 |
| agaaaattct tatgtttatg ttgattattg ggatgactca caagcattta ggaacatggt | 1080 |
| atatgtcagg tcattggcag caaatttaaa ttcagtaaag tgtagcggag gaaattataa | 1140 |
| ttttcaaata ccagttggtg catggccagt gatgagtgga ggtgcagtgt ctttacattt | 1200 |
| cgcaggagtc actttatcca ctcaatttac tgacttcgta tcacttaatt cgttaagatt | 1260 |
| tagattcagt ttaaccgttg aagagccacc gttttcaatt tcacgtacac gtgtgtcagg | 1320 |
| attgtacggg ctaccagcat tcaatccgaa taacggacat gaatattatg aaatagctgg | 1380 |
| gagattttct cttatttcat tagtgtcgtc taatgacgat tatcaaactc caatcatgaa | 1440 |
| ttcagttaca gtgcgacaag atcttgaacg tcaactaggt gatttaaggg aggaattcaa | 1500 |
| ttccttatca caagaaatag caatgacaca attgatagat ttagcattat tgccattaga | 1560 |

-continued

```
tatgttttcc atgttttcag gtattaaaag cacaattgac gtagccaaat caatggtcac    1620
aaaggtgatg aaaaagttta agaaatcagg attagctaca tcaatctctg aattgactgg    1680
atcattatca aacgctgctt catcagtttc cagaagttca tctattagat ctaacatatc    1740
atccatatca gtgtggacgg atgtttccga acaaatagcg ggttcgtcag actccgttag    1800
gaacatttcc acgcaaacat cagctattag taaaagattg cgactacgcg aaattactac    1860
acaaactgaa ggtatgaatt ttgatgatat ttcagcggca gtccttaaaa ctaaaataga    1920
tagatcaact cacataagcc cagatacatt accagacata ataactgagt catctgaaaa    1980
gtttatacca aaacgagctt atagagttat aaaagatgat gaagtgatgg aagctgacgt    2040
ggatgggaag ttctttgcat ataaagttgg cacttttgaa gaagtaccat ttgacgtaga    2100
taaatttatt gatttggtaa ccgattctcc tgtaatttca gctataattg atttttaagac   2160 gttgaagaat ttaaacgaca attatggtat aacgcgatct caagcgttag acttaatcag    2220
atctgatccc agagttttac gtgattttat caaccagaat a                        2261

<210> SEQ ID NO 4
<211> LENGTH: 2269
<212> TYPE: DNA
<213> ORGANISM: Human rotavirus
<220> FEATURE:
<221> NAME/KEY: gene
<222> LOCATION: (1)..(2269)
<223> OTHER INFORMATION: VP4 gene of human rotavirus CAU 214 strain

<400> SEQUENCE: 4 cccccttag acagctactc actaattcat acacagttga attatcagat gaaattaata     60
caattggatc agaaaaaagt caaaatgtaa cgattaatcc cggaccgttt gctcaaacaa    120
attatgcacc agtgacttgg agtcatgggg aagtgaatga ttcgacaacg atagagccag    180
tactcgatgg tccttatcaa ccaacaaatt ttaagccacc aaacgattac tggatatatt    240
tgaatccaac taatcaacaa gttgtattag agggtactaa taatactgat atttgggttg    300
ctttattact tgttgaacca aacgtaacca atcaaagtag acaatacaca ttatttggag    360
aaatgaaaca aattactgta gaaaataaca caaacaaatg gaaattcttc gaaatgttca    420
gaagtaatgt taatgctgaa tttcaacata gcgcacatt aacgtcagac actaaaattag    480 ctgggtttat gaaattttat aatagtgttt ggactttcca cggtgaaacg ccgcatgcta    540
caactgatta ctcgtcaact tcaaatttat ctgaagtaca aactgtaata catgttgagt    600
tttatataat accaagatcg caagaatcta agtgtagtga atacataaat actgggttac    660
caccaatgca gaatacaagg aatatagttc cagttgcgtt atcagctaga tcagtgactt    720
atcaacgtgc tcaggttaat gaggatatca ttatatcaaa gacatcgttg tggaaagaaa    780
tgcaatataa cagagacatt ataataaggt ttaaatttaa taatagtata gtaaaacttg    840
gtgggctagg ttataaatgg tcagaaattt cgtttaaagc ggctaattat cagtacagtt    900
acttgcgaga tggagagcaa gttacggcac atactacttg ttcagtcaat ggtgtgaata    960
actttagtta taatggagga tcactaccaa ctgattttag tgtatcaaga tatgaagtga    1020
ttaaagaaaa ttcttatgtt tatgttgatt attgggatga ctcacaagca tttaggaaca    1080
tggtatatgt caggtcattg gcagcaaatt taaattcagt aaagtgtagc ggaggaaatt    1140
ataattttca aataccagtt ggtgcatggc cagtgatgag tggaggtgca gtgtctttac    1200
atttcgcagg agtcacttta tccactcaat ttactgactt cgtatcactt aattcgttaa    1260
gatttagatt cagtttaacc gttgaagagc caccgttttc aattttacgt acacgtgtgt    1320
```

```
caggattgta cgggctacca gcattcaatc cgaataacgg acatgaatat tatgaaatag   1380
ctgggagatt ttctcttatt tcattagtgc cgtctaatga cgattatcaa acttcaatca   1440
tgaattcagt tacagtgcga caagatcttg aacgtcaact aggtgattta agggaggaat   1500
tcaattcctt atcacaagaa atagcaatga cacaattgat agatttagca ttattgccat   1560
tagatatgtt ttccatgttt tcaggtatta aaagcacaat tgacgtagcc aaatcaatgg   1620
tcacaaaggt gatgaaaaag tttaagaaat caggattagc tacatcaatc tctgaattga   1680
ctggatcatt atcaaacgct gcttcatcag tttccagaag ttcatctatt agatctaaca   1740
tatcatccat atcagtgtgg acggatgttt ccgaacaaat agcgggttcg tcagactccg   1800
ttaggaacat ttccacgcaa acatcagcta ttagtaaaag attgcgacta cgcgaaatta   1860
ctacacaaac tgaaggtatg aattttgatg atatttcagc ggcagtcctt aaaactaaaa   1920
tagatagatc aactcacata agcccagata cattaccaga cataataact gagtcatctg   1980
aaaagtttat accaaaacga gcttatagag ttataaaaga tgatgaagtg atggaagctg   2040
acgtggatgg gaagttcttt gcatataaag ttggcacttt tgaagaagta ccatttgacg   2100
tagataaatt tattgatttg gtaaccgatt ctccctgtaat ttcagctata attgatttta   2160
agacgttgaa gaatttaaac gacaattatg gtataacgcg atctcaagcg ttagacttaa   2220
tcagatctga tcccagagtt ttacgtgatt ttatcaacca gaataatcc                2269

<210> SEQ ID NO 5
<211> LENGTH: 743
<212> TYPE: DNA
<213> ORGANISM: Human rotavirus
<220> FEATURE:
<221> NAME/KEY: gene
<222> LOCATION: (1)..(743)
<223> OTHER INFORMATION: NSP 4 gene of human rotavirus CAU 195 strain

<400> SEQUENCE: 5
ggcttttaaa aagttctgtt ccgagagagc gcgtgcggaa agatggataa gcttgccgac    60
ctcaactaca cattgagtgt aatcactta atgaatgaca cattgcattc tataattcag   120 gacccctggaa tggcgtattt tccatatatt gcatctgttc taacagtttt gttcacatta   180
cataaagctt caattccaac aatgaaaata gcattaaaaa cgtcaaaatg ttcatacaaa   240
gtgatcaagt attgtatagt cacaattatt aatactcttt taaaattggc aggatataaa   300
gaacaagtta ctactaaaga cgaaattgag cgacagatgg atagaattgt aaaagagatg   360
agacgtcagc tggaaatgat tgataaatta actactcgtg aaattgaaca agttgaattg   420
cttaaacgta tacatgacaa tttaataact agaccagctg atattgtaga tatgacgaag   480
gaatttaatc agaagaatat aaaaacgctg gatgagtggg agagcggaaa aaatccatat   540
gaaccgatag aagtgactgc atctatgtga gaggttgagt tgccgtcgtc tgtcttcgga   600
agcggcggaa ctctttaccg caagcccat tggacctgat gattgactga gaagccacag   660
tcaatcatat cgcgtgtggc tcagccttaa tcccgtttga ccaatccagc gaatgttgga   720
cgttaatgga aggaatggtc taa                                           743

<210> SEQ ID NO 6
<211> LENGTH: 732
<212> TYPE: DNA
<213> ORGANISM: Human rotavirus
<220> FEATURE:
<221> NAME/KEY: gene
<222> LOCATION: (1)..(732)
<223> OTHER INFORMATION: NSP 4 gene of human rotavirus CAU 214 strain
```

-continued

<400> SEQUENCE: 6

```
tttaaaaagt ctgttccgag agagcgcgtg cggaaagatg gataagcttg ccgacctcaa    60
ctacacattg agtgtaatca ctttaatgaa tgacacattg cagtctataa ttcaggaccc   120
tggaatggcg tattttccat atattgcatc tgttctaaca gttttgttca cattacataa   180
agcttcaatt ccaacaatga aaatagcatt aaaaacgtca aaatgttcat acaaagtgat   240
caagtattgt atagtcacaa ttattaatac tcttttaaaa ttggcaggat ataaagaaca   300
agttactact aaagacgaaa ttgagcgaca gatggataga attgtaaaag agatgagacg   360
tcagctggaa atgattgata aattaactac tcgtgaaatt gaacaagttg aattgcttaa   420
acgtatacat gacaatttaa taactagacc agctgatatt gtagatatga cgaaggaatt   480
taatcagaag aatataaaaa cgctggatga gtgggagagc ggaaaaaatc catatgaacc   540
gatagaagtg actgcatcta tgtgagaggt tgagttgccg tcgtctgtct tcggaagcgg   600
ctggctctct ttaccgcaag ccccattgga cctgatgatt gactgagaag ccacagtcaa   660
tcatatcgcg tgtggctcag ccttaatccc gtttgaccaa tccagcgaat gttggacgtt   720
aatggaagga at                                                       732
```

<210> SEQ ID NO 7
<211> LENGTH: 27
<212> TYPE: DNA
<213> ORGANISM: Artificial Sequence
<220> FEATURE:
<223> OTHER INFORMATION: Synthetic construct

<400> SEQUENCE: 7

```
ggctttaaag agagaatttc cgtctgg                                        27
```

<210> SEQ ID NO 8
<211> LENGTH: 27
<212> TYPE: DNA
<213> ORGANISM: Artificial Sequence
<220> FEATURE:
<223> OTHER INFORMATION: Synthetic construct

<400> SEQUENCE: 8

```
ggtcacatca tacaattcta atctaag                                        27
```

<210> SEQ ID NO 9
<211> LENGTH: 22
<212> TYPE: DNA
<213> ORGANISM: Artificial Sequence
<220> FEATURE:
<223> OTHER INFORMATION: Synthetic construct

<400> SEQUENCE: 9

```
tggcttcgcc attttataga ca                                             22
```

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10

```
atttcggacc attttataacc                                               20
```

<210> SEQ ID NO 11
<211> LENGTH: 22
<212> TYPE: DNA

```
<213> ORGANISM: Artificial Sequence
<220> FEATURE:
<223> OTHER INFORMATION: Synthetic construct

<400> SEQUENCE: 11
tggcttcgcc attttataga ca                                            22

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
ggtcacacta agaccattcc                                               20
```